United States Patent
Nappa et al.

(10) Patent No.: US 7,524,999 B2
(45) Date of Patent: Apr. 28, 2009

(54) PROCESS FOR THE PRODUCTION OF 1,1,1,3,3,3-HEXAFLUOROPROPANE

(75) Inventors: Mario Joseph Nappa, Newark, DE (US); Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 42 days.

(21) Appl. No.: 11/792,644

(22) PCT Filed: Dec. 19, 2005

(86) PCT No.: PCT/US2005/046264

§ 371 (c)(1),
(2), (4) Date: Jun. 7, 2007

(87) PCT Pub. No.: WO2006/069105

PCT Pub. Date: Jun. 29, 2006

(65) Prior Publication Data

US 2008/0108853 A1 May 8, 2008

Related U.S. Application Data

(60) Provisional application No. 60/638,277, filed on Dec. 22, 2004.

(51) Int. Cl.
*C07C 17/00* (2006.01)
*C07C 17/20* (2006.01)

(52) U.S. Cl. .................. 570/169; 570/161; 570/164; 570/170

(58) Field of Classification Search .............. 570/169, 570/170, 161, 164
See application file for complete search history.

(56) References Cited

U.S. PATENT DOCUMENTS

| | | | |
|---|---|---|---|
| 3,554,887 A | 1/1971 | Feehs et al. | |
| 5,414,165 A | 5/1995 | Nappa et al. | |
| 5,545,774 A | 8/1996 | Rao | |
| 5,573,654 A | 11/1996 | Chebyrkov et al. | |
| 5,811,604 A | 9/1998 | Benson et al. | |
| 6,066,769 A | 5/2000 | Nappa et al. | |
| 6,291,730 B1 | 9/2001 | Baker et al. | |
| 2007/0265368 A1 | 11/2007 | Rao et al. | |
| 2008/0015277 A1 | 1/2008 | Rao et al. | |
| 2008/0076950 A1 | 3/2008 | Rao et al. | |
| 2008/0149472 A1 | 6/2008 | Rao et al. | |

FOREIGN PATENT DOCUMENTS

| | | |
|---|---|---|
| EP | 0 670 294 A2 | 9/1995 |
| EP | 0 670 294 A3 | 1/1996 |

OTHER PUBLICATIONS

J. Chen et al., Kinetic and Mechanistic for Reactions of CF3CH2CHF22 (HFC-245fa) Initiated by H-Atom Abstraction Using Atomic Chlorine, J. Phys. Chem. A., 1997, vol. 101:2648-2653.

*Primary Examiner*—Jafar Parsa

(57) ABSTRACT

A process for the preparation of 1,1,1,3,3,3-hexafluoropropane is disclosed. The process involves (a) contacting at least one halopropane of the formula $CF_3CH_2CH_yX_{3-y}$ (where each X is independently F, Cl or Br, and y is 3, 2, or 1) with $Cl_2$#191 in the presence of light or a free radical initiator to produce a mixture comprising $CF_3CH_2CCl_yX_{3-y}$; (b) contacting the $CF_3CH_2CCl_yX_{3-y}$ produced in step (a) with HF, optionally in the presence of a fluorination catalyst, to produce a product mixture comprising $CF_3CH_2CF_3$; and (c) recovering $CF_3CH_2CF_3$ from the mixture produced in step (b).

20 Claims, No Drawings

PROCESS FOR THE PRODUCTION OF 1,1,1,3,3,3-HEXAFLUOROPROPANE

This application represents a national filing under 35 U.S.C. 371 of International Application No. PCT/US2005/046264 filed Dec. 19, 2005, and claims priority of U.S. Provisional Application No. 60/638,277 filed Dec. 22, 2004.

FIELD OF THE INVENTION

The present invention relates to the synthesis of 1,1,1,3,3,3-hexafluoropropane.

BACKGROUND

Commercial methods for the preparation of 1,1,1,3,3,3-hexafluoropropane ($CF_3CH_2CF_3$ or HFC-236fa), a fire extinguishant and refrigerant, involve fluorination of 1,1,1,3,3,3-hexachloropropane ($CCl_3CH_2CCl_3$ or HCC-230fa) in the liquid phase (see for e.g., U.S. Pat. No. 6,291,730), in the vapor phase (see e.g., U.S. Pat. Nos. 5,414,165 and 5,545,774), or a combination of liquid and vapor phase processes (see U.S. Pat. No. 6,066,769). U.S. Pat. No. 5,573,654 reports the preparation of HFC-236fa by the reaction of perfluoroisobutylene with triethylamine and water.

SUMMARY OF THE INVENTION

This invention provides a process for the preparation of 1,1,1,3,3,3-hexafluoropropane. The process comprises (a) contacting at least one halopropane of the formula $CF_3CH_2CH_yX_{3-y}$ (where each X is independently selected from the group consisting of F, Cl and Br, and y is 3, 2, or 1) with chlorine ($Cl_2$) in the presence of light or a free radical initiator to produce a mixture comprising $CF_3CH_2CCl_yX_{3-y}$; (b) contacting the $CF_3CH_2CCl_yX_{3-y}$ produced in step (a) with HF, optionally in the presence of a fluorination catalyst, to produce a product mixture comprising $CF_3CH_2CF_3$; and (c) recovering $CF_3CH_2CF_3$ from the mixture produced in step (b).

DETAILED DESCRIPTION

This invention provides a process for the preparation of 1,1,1,3,3,3-hexafluoropropane ($CF_3CH_2CF_3$, HFC-236fa) from readily available starting materials.

In step (a) of the process of this invention, one or more halopropane compounds $CF_3CH_2CH_yX_{3-y}$, where each X is independently F, Cl, or Br, and y is 3, 2, or 1, are contacted with chlorine ($Cl_2$) in the presence of an initiator. Typically, the reaction of halopropane starting material(s) with chlorine is carried out in a reaction zone operated to provide substantial substitution of chlorine for the end-carbon hydrogens of the halopropane starting material(s) without substantial replacement of hydrogens on the middle carbon. Typically at least 90%, and preferably greater than 95%, of the hydrogens of the $CF_3CH_2CH_yX_{3-y}$ starting material replaced during step (a) are end carbon hydrogens. Free radical initiators such as peroxides or azo compounds may be employed. Preferably, chlorine radicals are generated by the action of light on $Cl_2$ (i.e., photochlorination is preferably used).

Suitable halopropane starting materials for step (a) include $CF_3CH_2CHF_2$ (HFC-245fa), $CF_3CH_2CHClF$ (HCFC-244fa), $CF_3CH_2CHCl_2$ (HCFC-243fa), $CF_3CH_2CH_2Cl$ (HCFC-253fb), $CF_3CH_2CH_2Br$ (HCFC-253fbB), $CF_3CH_2CH_2F$ (HFC-254fb), and $CF_3CH_2CH_3$ (HFC-263fb). Due to their availability, $CF_3CH_2CHF_2$ (HFC-245fa), $CF_3CH_2CH_2Cl$ (HCFC-253fb), and $CF_3CH_2CH_3$ (HFC-263fb) are generally preferred.

1,1,1,3,3-Pentafluoropropane (HFC-245fa) may be prepared by fluorination of HCC-240fa as described in U.S. Pat. No. 6,291,730. HCFC-253fb may be prepared by fluorination of 1,1,1,3-tetrachloropropane as disclosed in U.S. Pat. No. 4,078,007. HFC-263fb may be prepared by hydrogenation of 3,3,3-trifluoropropene as disclosed by Haszeldine in *Journal of the Chemical Society*, 1952, page 2510.

The photochlorination of the halopropane starting materials of the formula $CF_3CH_2CH_yX_{3-y}$ may be carried out in either the liquid or the vapor phase. For vapor phase photochlorination, initial contact of the starting materials with $Cl_2$ may be a continuous process in which one or more starting materials are vaporized (optionally in the presence of an inert carrier gas, such as nitrogen, argon, or helium) and contacted with chlorine vapor in a reaction zone. A suitable photochlorination reaction zone is one in which light having a wavelength of from about 250 nm to about 400 nm can irradiate the reaction components for a time sufficient to convert at least a portion of the halopropane starting materials to $CF_3CH_2CCl_yX_{3-y}$. The source of light may be any one of a number of arc or filament lamps known in the art. Light having the desired wavelength may introduced into the reaction zone by a number of means. For example, the light may enter the reaction zone through a lamp well or window fabricated from a material suitably transparent to light having a wavelength of from about 250 nm to about 400 nm. Likewise, the walls of the reaction zone may be fabricated from such a material so that at least a portion of the light used for the photochlorination can be transmitted through the walls. Examples of suitable materials include quartz, glass, or fluoropolymers such as poly(tetrafluoroethylene) (e.g., Teflon® fluoropolymer), copolymers of perfluoro(alkyl vinyl ethers) (e.g., polyfluoroalkoxy resins such as Teflon® PFA fluoropolymer), and functionalized copolymers of terminally functionalized perfluoro(alkyl vinyl ethers) (e.g., perfluorosulfonic acid resins such as Nafion® fluoropolymer). Further details of photochlorination using polymeric materials such as Teflon® fluoropolymer, Teflon® PFA fluoropolymer, and Nafion® fluoropolymer are disclosed in U.S. patent application Ser. Nos. 60/638289, 60/638292, 60/638290 and 60/638293 all of which were filed Dec. 22, 2004, and are incorporated herein by reference. Of note are embodiments where the chlorination step (a) is carried out in a reactor wherein a portion of the reactor wall is fabricated from poly(tetrafluoroethylene), a copolymer of perfluoro(alkyl vinyl ether), or a functionalized copolymer of a terminally functionalized perfluoro(alkyl vinyl ether), and light is transmitted through said polymeric portion.

The portion of the reactor wall fabricated from such polymeric materials may be limited to a fraction of the reactor wall (e.g., a window of the polymeric material positioned in a reactor principally fabricated from another material) or may constitute all or essentially all of the reactor wall (e.g., a tube reactor fabricated from the polymeric material).

Alternatively, the process of the invention may be carried out in the liquid phase by feeding $Cl_2$ to a reactor containing the halopropane starting materials. Suitable liquid phase reactors include vessels fabricated from glass in which an external lamp is directed toward the reactor and metal or glass-lined metal reactors having one or more wells or windows for introducing light having a suitable wavelength. Also suitable are fluoropolymer-lined metal reactors having one or more wells or windows for introducing light having a suitable wavelength. Preferably the reactor is provided with a condenser or other means of keeping the halopropane starting materials being irradiated to be in the liquid state in the reactor while permitting the hydrogen chloride (HCl) released during the chlorination to escape the reactor.

In some embodiments it may be advantageous to conduct the photochlorination in the presence of a solvent capable of dissolving one or more of the halopropane starting materials and/or step (a) products. Preferred solvents include those that do not have easily replaceable hydrogen substituents. Examples of solvents suitable for step (a) include carbon tetrachloride, 1,1-dichlorotetrafluoroethane, 1,2-dichlorotetrafluoroethane, 1,1,2-trichlorotrifluoroethane, benzene, chlorobenzene, dichlorobenzene, fluorobenzene, and difluorobenzene.

Suitable temperatures for the photochlorination of the halopropane starting materials of the formula $CF_3CH_2CH_yX_{3-y}$ are within the range of from about $-20°$ C. to about $60°$ C. Preferred temperatures are typically within the range of from about $0°$ C. to about $40°$ C. In the liquid phase embodiment of step (a), it is convenient to control the reaction temperature so that starting material is primarily in the liquid phase; that is, at a temperature that is below the boiling point of the step (a) halopropane starting material(s) and product(s).

The pressure of step (a) in a liquid phase process is not critical so long as the liquid phase is maintained. Unless controlled by means of a suitable pressure-regulating device, the pressure of the system increases as hydrogen chloride is formed during step (a) by replacement of hydrogen substituents in the starting material by chlorine substituents. In a continuous or semi-batch process it is possible to set the pressure of the reactor in such a way that the HCl produced in the reaction is vented from the reactor (optionally through a packed column or condenser). Typical reactor pressures are from about 14.7 psig (101.3 kPa) to about 50 psig (344.6 kPa).

The amount of chlorine ($Cl_2$) fed to the reactor is based on the value of y in $CF_3CH_2CH_yX_{3-y}$. The ratio of $Cl_2$ to halopropane starting material is typically the stoichiometric amount required to substitute the hydrogen in the $CH_yX_{3-y}Y$ group with a chlorine atom. For example, when y is 3, the molar ratio of $Cl_2$ to $CF_3CH_2CH_yX_{3-y}$ is preferably about 3:1; when y is 2, the molar ratio of $Cl_2$ to $CF_3CH_2CH_yX_{3-y}$ is preferably about 2:1; and when y is 1, the molar ratio of $Cl_2$ to $CF_3CH_2CH_yX_{3-y}$ is preferably about 1:1. A slight excess of chlorine over the stoichiometric amount may be desirable to facilitate conversion, but feeding a large excess chlorine to the reactor can result in a higher degree of halogenation in the products than is desirable.

Examples of compounds that can be produced in step (a), particularly by photochlorination, include $CF_3CH_2CCl_3$ (HCFC-233fb, produced from $CF_3CH_2CH_yX_{3-y}$ starting material where y is 3, 2, or 1 and X is Cl), $CF_3CH_2CBrCl_2$ (HCFC-233fbB, produced from $CF_3CH_2CH_yX_{3-y}$ starting material where y is 2 and X is Br), $CF_3CH_2CCl_2F$ (HCFC-234fb, produced from $CF_3CH_2CH_yX_{3-y}$ starting material where y is 2 and X is F, or where y is 1, one X is Cl and the other X is F), and $CF_3CH_2CClF_2$ (HCFC-235fa, produced from $CF_3CH_2CH_yX_{3-y}$ starting material where y is 1 and X is F).

Under-chlorinated halopropane by-products that may be formed include compounds in which the value of y in $CF_3CH_2CH_yX_{3-y}$ has been reduced from 3 to 2, from 3 to 1, or from 2 to 1.

Over-chlorinated halopropane by-products that may be produced include halopropanes of the formula $CF_3CH_{2-w}Cl_wCCl_yX_{3-y}$ where w=1 or 2, such as for example, $CF_3CHClCClF_2$ (HCFC-225da), $CF_3CCl_2CClF_2$ (CFC-215aa), $CF_3CHClCCl_2F$ (HCFC-224db), $CF_3CCl_2CCl_2F$ (CFC-214ab), $CF_3CHClCCl_3$ (HCFC-223ab), and $CF_3CCl_2CCl_3$ (CFC-213ab).

If desired, the effluent from step (a) may be subjected to one or more purification steps where the desired product, $CF_3CH_2CCl_yX_{3-y}$, is separated from HCl, under-chlorinated halopropane by-products, unreacted halopropane starting materials, and over-chlorinated halopropane by-products by distillation. In one embodiment of the invention unreacted halopropane starting materials and under-chlorinated halopropane by-products may be recovered and returned to step (a).

In step (b) of the process of the invention, the $CF_3CH_2CCl_yX_{3-y}$ produced in step (a) is contacted with HF, optionally in the presence of a fluorination catalyst, to produce a mixture comprising $CF_3CH_2CF_3$. Step (b) of the process of the invention may take place in either liquid or the vapor phase.

In the liquid phase embodiment of step (b), the reactor effluent from step (a) or the separated $CF_3CH_2CCl_yX_{3-y}$ produced in step (a), is contacted with anhydrous hydrogen fluoride (HF) to form a mixture of fluorinated compounds. The contacting of $CF_3CH_2CCl_yX_{3-y}$ and HF may be conducted in the liquid phase in one of several ways. The process of the invention may be conducted in batch, semi-continuous, or continuous modes. In the batch mode, the $CF_3CH_2CCl_yX_{3-y}$ step (b) starting material and hydrogen fluoride are combined in an autoclave or other suitable reaction vessel and heated to the desired temperature. Preferably, liquid step (b) starting material of the formula $CF_3CH_2CCl_yX_{3-y}$ is fed to a reactor containing liquid HF, or a liquid mixture of HF and fluorinated compounds formed by reacting HF with $CF_3CH_2CCl_yX_{3-y}$ starting material, held at the desired reaction temperature. Alternatively, liquid HF may be fed to a reactor containing $CF_3CH_2CCl_yX_{3-y}$ starting material, or a mixture of $CF_3CH_2CCl_yX_{3-y}$ starting material and a mixture of fluorinated compounds formed by reacting HF with the $CF_3CH_2CCl_yX_{3-y}$ starting material.

In another embodiment, both HF and $CF_3CH_2CCl_yX_{3-y}$ starting material may be fed concurrently as liquids in the desired stoichiometric ratio to a reactor containing a mixture of HF and fluorinated compounds formed by reacting HF with $CF_3CH_2CCl_yX_{3-y}$.

In the liquid phase embodiment of step (b) of the process, the $CF_3CH_2CCl_yX_{3-y}$ starting materials are preferably reacted with HF in the presence of fluorination catalysts selected from the halides, oxides, or oxyhalides of one or more metal compounds. Said metals may be selected from the group consisting of boron, aluminum, tin, titanium, vanadium, iron, zinc, arsenic, antimony, molybdenum, tungsten, niobium, and tantalum, and mixtures thereof. Said halides, oxides, or oxyhalides of one or more metal compounds may optionally be supported on carbon. Of note are fluorination catalyst compositions selected from the group consisting of $AlF_3$, $BF_3$, $FeCl_{3-a}F_a$ (where a is 0 to 3), $FeZ_3$ (where Z is halogen) supported on carbon, $SbCl_{3-a}F_a$, $AsF_3$, $MCl_{5-b}F_b$ (where b is 0 to 5 and M is Sb, Nb, Ta, or Mo), and $M'Cl_{4-c}F_c$ (where c is 0 to 4, and M' is Sn, Ti, Zr, or Hf). Preferred fluorination catalyst compositions for the liquid phase embodiment of step (b) are those containing metal halides selected from the group antimony, tin, niobium, and tantalum.

Other fluorination catalyst compositions useful for liquid phase step (b) embodiments include halides, fluorosulfonates or triflates of antimony, molybdenum, niobium, tantalum, tin or titanium as disclosed in U.S. Pat. No. 5,773,637.

The temperature of the liquid phase embodiment of step (b) can be in the range of $50°$ C. to $175°$ C., preferably, $60°$ C. to 150° C. The pressure is selected so that the reaction medium is maintained in the liquid state.

The pressure of the system increases as hydrogen chloride or hydrogen bromide are formed by replacement of chlorine or bromine substituents for fluorine subsituents in the $CF_3CH_2CCl_yX_{3-y}$ starting materials and as the volatility of the organic components increases due to the formation of $CF_3CH_2CF_3$. In a continuous process it is possible to set the pressure of the reactor in such a way that the HCl or HBr liberated by the reaction is vented from the reactor. Typical reaction pressures are from about 20 psig (137.8 kPa) to about 1000 psig (6891 kPa).

The molar ratio of HF to $CF_3CH_2CCl_yX_{3-y}$ starting materials employed in the liquid phase embodiment of step (b) is typically from about 1:1 to about 100:1, preferably from about 3:1 to about 50:1 and most preferably from about 3:1 to about 30:1.

The step (b) reaction of HF with $CF_3CH_2CCl_yX_{3-y}$ can also be carried out in the vapor phase (e.g., in a heated tubular reactor). For tubular reactors, a number of reactor configurations are possible, including horizontal or vertical orientation of the reactor and different modes of contacting the starting halopropanes with HF. Preferably the HF is substantially anhydrous.

The step (b) starting material(s) may be fed to a reactor containing a fluorination catalyst. For example, the halopropane starting material(s) may be initially vaporized and the vaporized starting materials and HF may be directly fed to a reaction zone containing a fluorination catalyst as gas(es).

Alternatively, the step (b) halopropane starting material(s) may be contacted with HF in a pre-reactor. The pre-reactor may be empty (i.e., unpacked), but is preferably filled with a suitable packing such as Monel™ or Hastelloy™ nickel alloy turnings or wool, or other material inert to HCl and HF which allows efficient mixing (and partial reaction) of the step(b) halopropane starting material(s) and HF vapor.

When feeding the halopropane starting material(s) to the pre-reactor as liquid(s), it is preferable for the pre-reactor to be oriented vertically with $CF_3CH_2CCl_yX_{3-y}$ entering the top of the reactor and pre-heated HF vapor introduced at the bottom of the reactor.

Temperatures for the pre-reactor are typically within the range of from about 80° C. to about 250° C., and preferably are within the range of from about 100° C. to about 200° C. Under these conditions, for example, $CF_3CH_2CCl_3$ may be converted to a mixture containing predominantly $CF_3CH_2CCl_2F$. The starting material feed rate is ordinarily determined by the length and diameter of the reactor, the temperature, and the degree of fluorination desired within the pre-reactor. Slower feed rates at a given temperature will increase contact time and tend to increase the amount of conversion of the starting material and increase the degree of fluorination of the products. The term "degree of fluorination" means the extent to which fluorine atoms replace chlorine substituents in the $CF_3CH_2CCl_yX_{3-y}$ starting materials. For example, $CF_3CH_2CClF_2$ represents a higher degree of fluorination than $CF_3CH_2CCl_3$.

The molar ratio of HF fed to the pre-reactor, or otherwise to the reaction zone, to $CF_3CH_2CCl_yX_{3-y}$ starting material(s), is typically from about stoichiometric to about 50:1. The stoichiometric ratio depends on the average degree of fluorination of the halopropane starting material(s) and is typically based on formation of $CF_3CH_2CF_3$. For example, when y is 3, the stoichiometric ratio of HF to $CF_3CH_2CCl_yX_{3-y}$ is 3:1. If the average value of y in the halopropane starting materials is 2, the stoichiometric ratio of HF to $CF_3CH_2CCl_yX_{3-y}$ is 2:1. If the average value of y in the halopropane starting materials is 1, the stoichiometric ratio of HF to $CF_3CH_2CCl_yX_{3-y}$ is 1:1. Preferably, the molar ratio of HF to halopropane starting material is from about twice the stoichiometric ratio (based on formation of $CF_3CH_2CF_3$) to about 30:1. Higher ratios of HF to $CF_3CH_2CCl_yX_{3-y}$ may not be particularly beneficial. Lower ratios can result in reduced yields of $CF_3CH_2CF_3$.

In a preferred embodiment of step (b), the halopropane starting materials are vaporized, preferably in the presence of HF, and contacted with HF in a pre-reactor and the pre-reactor effluent is then contacted with the fluorination catalyst. If the preferred amount of HF is fed in the pre-reactor, additional HF is not required when the effluent from the pre-reactor contacts the fluorination catalyst.

Temperatures for catalytic fluorination of the $CF_3CH_2CCl_yX_{3-y}$ starting material (and/or the products formed in a pre-reactor) are typically within the range of from about 200° C. to about 450° C., and preferably are in the range of from about 250° C. to about 400° C., depending on the desired conversion of the starting material and the activity of the catalyst. Reactor temperatures greater than about 400° C. may result in the formation of small amounts of unsaturated by-products. Reactor temperatures below about 240° C. may result in a substantial yield of products with a degree of fluorination less than six (i.e., underfluorinates).

Reactor pressures for vapor phase embodiments of step (b) may be in the range of from about 1 to about 30 atmospheres. Reactor pressures of about 5 atmospheres to about 20 atmospheres may be advantageously employed to facilitate separation of HCl from other reaction products after the fluorination.

Preferably, vapor phase embodiments of step (b) are carried out at least in part in a reactor that contains a catalyst. Catalysts which may be used in the preferred vapor phase embodiments of the invention include metals (including elemental metals, metal oxides, metal halides, and/or other metal salts); alumina; fluorided alumina; aluminum fluoride; metals supported on alumina; metals supported on aluminum fluoride; magnesium fluoride supported on aluminum fluoride; metals supported on fluorided alumina; alumina supported on carbon; aluminum fluoride supported on carbon; fluorided alumina supported on carbon; metals supported on carbon; and mixtures of metals, aluminum fluoride, and graphite.

Suitable metals for use in catalyst compositions (optionally on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). Preferably when used on a support, the total metal content of the catalyst will be from about 0.1 to 20 percent by weight; typically from about 0.1 to 10 percent by weight.

Preferred fluorination catalysts include chromium catalysts (e.g., $Cr_2O_3$ by itself or with other metals such as magnesium halides or zinc halides on $Cr_2O_3$); chromium (III) halides supported on carbon; mixtures of chromium and magnesium (including elemental metals, metal oxides, metal halides, and/or other metal salts) optionally on graphite; and mixtures of chromium and cobalt (including elemental metals, metal oxides, metal halides, and/or other metal salts) optionally on graphite, alumina, or aluminum halides such as aluminum fluoride.

Catalysts comprising chromium are well known in the art (see e.g., U.S. Pat. No. 5,036,036). Chromium supported on alumina can be prepared as described in U.S. Pat. No. 3,541,834. Chromium supported on carbon can be prepared as described in U.S. Pat. No. 3,632,834. Catalysts comprising chromium and magnesium may be prepared as described in Canadian Patent No. 2,025,145. Other metals and magnesium optionally on graphite can be prepared in a similar manner to the latter patent.

Preferred chromium catalysts comprise trivalent chromium. Of note is $Cr_2O_3$ prepared by pyrolysis of $(NH_4)_2Cr_2O_7$, $Cr_2O_3$ having a surface area greater than about 200 $m^2$/g, and chromium chloride supported on carbon having a surface area greater than about 200 $m^2$/g some of which are commercially available.

The $Cr_2O_3$ catalyst prepared by the pyrolysis of ammonium dichromate suitable for the process of this invention can be prepared by any method known to the art including those disclosed in U. S. Pat. Nos. 4,843,181 and 5,036,036 which are hereby incorporated herein by reference.

Typically, the catalyst compositions will be pretreated with a fluorinating agent prior to use as catalysts for changing the fluoride content of halogenated carbon compounds. Typically this fluorinating agent is HF though other materials may be used such as sulfur tetrafluoride, boron trifluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pretreatment is not essential.

The product of the step (b) fluorination includes $CF_3CH_2CF_3$ (HFC-236fa). Halopropane by-products having lower degrees of fluorination than HFC-236fa that may be present in a product mixture of step (b) include $CF_3CH_2CClF_2$ (HCFC-235fa) and $CF_3CH_2CCl_2F$ (HCFC-234fb). In one embodiment of this invention, these under fluorinated by-products may be returned to the reaction zone of step (b).

Halopropane by-products having higher degrees of halogenation than HFC-236fa that may be present in the product of step (b) include $CF_3CHClCF_3$ (HCFC-226da).

Halopropene by-products that may be present in the product of step (b) include $CF_3CH=CF_2$ (HFC-1225zc), isomers of $C_3HClF_4$ (HCFC-1224) such as $CF_3CH=CClF$ (HCFC-1224zb), isomers of $C_3HCl_2F_3$ (HCFC-1223) such as $CF_3CH=CCl_2$ (HCFC-1223za), or $CF_3CH=CHCl$ (HCFC-1233zd).

In step (c) of the process of the invention, the effluent from the reaction zone of step (b) may be delivered to one or more distillation columns in which HCl, HF, halopropane by-products having lower degrees of fluorination than HFC-236fa, halopropane by-products having higher degrees of halogenation than HFC-236fa, and halopropene by-products are separated from HFC-236fa and/or the azeotrope of HFC-236fa with HF. The HFC-236fa can be recovered from the HF azeotrope by methods known in the art, such as extractive distillation.

The $CF_3CH_2CF_3$ recovered from step (c) may also be separated from HF by washing the mixture with water optionally followed by washing with a dilute solution or dispersion of an aqueous base such as caustic.

Alternatively, HF may be removed from HFC-236fa by reaction as disclosed in U.S. Pat. No. 6,224,781.

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

| LEGEND | |
|---|---|
| 113 is $CClF_2CCl_2F$ | 113a is $CF_3CCl_3$ |
| 133a is $CF_3CH_2Cl$ | 215aa is $CF_3CCl_2CClF_2$ |
| 225da is $CF_3CHClCClF_2$ | 234 is $C_3H_2Cl_2F_4$ |
| 234fb is $CF_3CH_2CCl_2F$ | 235fa is $CF_3CH_2CClF_2$ |
| 236fa is $CF_3CH_2CF_3$ | 245fa is $CF_3CH_2CHF_2$ |
| 1223 is $C_3HCl_2F_3$ | 1224 is $C_3HClF_4$ |
| 1225zc is $CF_2=CHCF_3$ | |

Example 1

Chlorination of HFC-245fa in Carbon Tetrachloride

A 35 mL Pyrex™ glass flanged reactor equipped with internal cooling coils, a Claisen adapter, condenser, a TC well, a PTFE-coated stirring bar, and a chlorine inlet tube was charged with 33.0 g of carbon tetrachloride. The top of the condenser was connected in series to a bubbler containing Krytox® oil and a KOH scrubber. The reactor cooling coil and condenser were connected to a small chiller recirculating water/ethylene glycol at a temperature of about −9° C. After the reactor was cooled, about 9 g (0.067 mole) of HFC-245fa were added to the reactor from a cylinder. The reactor was purged with nitrogen and irradiated with a 275W Sylvania™ sunlamp. Chlorine gas was fed subsurface into the reactor solution from a rotameter at a rate of about 20 sccm ($3.4\times10^{-7}$ $m^3$/s). The temperature in the reactor during the chlorination was about 3-5° C. After 1 hour the chlorine feed and irradiation were stopped. Analysis of the reaction solution by GC-MS indicated that the product was substantially 235fa. After washing the product with aqueous 10% sodium bisulfite, a total of 32 g of product were obtained.

Example 2

Chlorination of HFC-245fa in the Absence of Solvent

Following the procedure described above, the 35 mL reactor was purged with nitrogen with cooling applied to the coils. The reactor was then charged with about 30 g (0.224 mole) of HFC-245fa. The reactor was purged briefly with nitrogen and then irradiated with a 275W Sylvania™ sunlamp. Chlorine gas was fed subsurface to the reactor from a rotameter at a rate of about 20 sccm ($3.4\times10^{-7}$ $m^3$/s); the temperature in the reactor during the chlorination was about 2-3° C. After about 3 hours, there was noticeable chlorine break-through; the chlorine feed and irradiation were then stopped. Analysis of the reaction product by GC-MS indicated that the product was about 97% 235fa. After washing the product with aqueous 10% sodium bisulfite, a total of 16 g of product were obtained. The reaction product was analyzed by GC-MS; the principal products are summarized in TABLE I.

TABLE I

HFC-245fa Photochlorination Products

| Code | Formula | GC Area % |
|---|---|---|
| HCFC-235fa | $CF_3CH_2CClF_2$ | 98.05 |
| CFC-215aa | $CF_3CCl_2CClF_2$ | 0.64 |
| HCFC-225da | $CF_3CHClCClF_2$ | 0.42 |
| HCFC-234 | $C_3H_2Cl_2F_4$ | 0.30 |

Examples 3-4

Chlorination of HFC-245fa in the Vapor Phase

A 91.4 cm length of Pyrex™ glass tubing was formed in a coil about 8 cm in diameter; the tubing had an inner diameter of 0.395 cm and a wall thickness of about 1.2 mm. Chlorine gas and HFC-245fa were co-fed to the coil at room temperature; the coil was irradiated with the 275 watt sunlamp. The residence time in the tube was approximately 17 seconds. The effluent from the tube was analyzed by gas chromatography; the results are summarized in the TABLE II.

TABLE II

| Ex. No. | Mole Ratio $Cl_2$/245fa | Product Analysis, GC Area % | | | | | | |
|---|---|---|---|---|---|---|---|---|
| | | 235fa | 245fa | 225da | 215aa | 234 | 133a | 113a |
| 3 | 1 | 88.5 | 11.0 | 0.2 | 0.05 | 0.02 | 0.01 | 0.1 |
| 4 | 2 | 98.4 | 0.2 | 0.6 | 0.5 | 0 | 0 | 0.3 |

Examples 5-6

Chlorination of HFC-245fa in the Vapor Phase

The Example above was repeated using a 91.4 cm length of Teflon™ PFA tubing which was formed in a coil about 14 cm in diameter; the tubing had an inner diameter of 0.32 cm and a wall thickness of about 1.6 mm. Chlorine gas and HFC-245fa were co-fed to the coil at room temperature; the coil was irradiated with the 275 watt sunlamp. The residence time in the tube was approximately 11 seconds. The effluent from the tube was analyzed by gas chromatography; the results are summarized in the TABLE III.

TABLE III

| Ex. No. | Mole Ratio $Cl_2$/245fa | Product Analysis, GC Area % | | | | | | |
|---|---|---|---|---|---|---|---|---|
| | | 235fa | 245fa | 225da | 215aa | 234 | 133a | 113a |
| 5 | 1 | 87.2 | 12.4 | 0.2 | 0.04 | 0.03 | 0.01 | 0.1 |
| 6 | 2 | 91.8 | 7.6 | 0.2 | 0.04 | 0 | 0.04 | 0.2 |

Example 7

Chlorination of HFC-245fa in the Vapor Phase

The Example above was repeated using a 45.7 cm length of Nafion™ tubing which was formed in a coil about 8 cm in diameter; the tubing had an inner diameter of 0.14 cm and a wall thickness of about 0.13 mm. Chlorine gas and HFC-245fa were co-fed to the coil at room temperature; the coil was irradiated with the 275 watt sunlamp. The residence time in the tube was approximately 6 seconds. The effluent from the tube was analyzed by gas chromatography; the results are summarized in the TABLE IV.

TABLE IV

| Ex. No. | Mole Ratio $Cl_2$/245fa | Product Analysis, GC Area % | | | | | | |
|---|---|---|---|---|---|---|---|---|
| | | 235fa | 245fa | 225da | 215aa | 234 | 133a | 113a |
| 7 | 1 | 13.3 | 86.2 | 0 | 0 | 0 | 0.4 | 0.01 |

Examples 8-9

Vapor Phase Fluorination of HCFC-235fa

A commercial sample of 20% $CrCl_3$ on carbon catalyst was used for this work. The preparation and activation procedure of this catalyst is described in U.S. Pat. No. 5,545,774.

The 20% $CrCl_3$ on carbon catalyst prepared above (3.12 g, 8 mL, 6 to 8 mesh, (2.36 to 3.35 mm)) was placed in a ⅝" (1.58 cm) diameter Inconel™ nickel alloy reactor tube heated in a fluidized sand bath. The catalyst was heated from 53° C. to 177° C. in a flow of nitrogen (50 sccm, $8.4 \times 10^{-7}$ m³/s) over the course of about one hour. HF was then admitted to the reactor at a flow rate of 50 sccm ($8.4 \times 10^{-7}$ m³/s). After 0.5 h the nitrogen flow was decreased to 20 sccm ($3.4 \times 10^{-7}$ m³s) and the HF flow increased to 80 sccm ($1.3 \times 10^{-8}$ m³/s). The reactor temperature was then gradually increased to 400° C. over 3 hours. At the end of this period, the HF flow was stopped and the reactor cooled to 175° C. under 20 sccm ($3.4 \times 10^{-7}$ m³/s) nitrogen flow. The results of the fluorination of HCFC-235fa at 250° C. and 300° C. are shown in TABLE IV below. The contact time was 20 seconds and the mole ratio of HF to HCFC-235fa was 6:1.

TABLE V

| Ex. No. | Temp | Product Analysis, GC Area % | | | | | | |
|---|---|---|---|---|---|---|---|---|
| | | 236fa | 235fa | 1225zc | 226da | 1224 | 1223 | 113 |
| 8 | 250 | 83.1 | 14.1 | 1.7 | 0.2 | 0.3 | 0.2 | 0.3 |
| 9 | 300 | 99.1 | 0.07 | 0.1 | 0.2 | 0.02 | 0 | 0.3 |

Examples 10-12

Vapor Phase Fluorination of a Mixture of HCFC-1223za, HFC-234fb, and HFC-232fa

Catalyst Activation

A 15 in×⅜ in Inconel® tube was filled with 1.64 grams (1.5 cc) of a high surface area chrome oxide gel catalyst (>200 m²/gm) ground to 20-30 mesh (0.60 to 0.85 mm). The catalyst was activated by first drying at 400° C. for 0.33 hours under a nitrogen purge (38 sccm, 6.3×10$^{-7}$ m$^3$s). The temperature was lowered to 300° C., and the HF flow was begun (15 sccm, 2.5×10$^{-7}$ m$^3$/s) and the nitrogen flow was reduced (25 sccm, 4.2×10$^{-7}$ m$^3$/s). After 35 minutes the temperature was raised to 325° C. for 60 minutes, to 350° C. for 60 minutes, 375° C. for 60 minutes, 400° C. for 60 minutes, and 425° C. for 60 minutes. After this period of 60 minutes at 425° C., the flow of HF was set to 26 sccm (4.3×10$^{-7}$ m$^3$/s) while the nitrogen flow was set to 16 sccm (4.2×10$^{-7}$ m$^3$/s). After 20 minutes, the HF flow was increased to 38 sccm (6.3×10$^{-7}$ m$^3$/s) and the nitrogen decreased to 11 sccm. After 20 minutes, the HF flow was maintained at 38 sccm (6.3×10$^{-7}$ m$^3$/s) while the nitrogen flow was decreased to 11 sccm (1.8×10$^{-7}$ m$^3$/s). After 20 minutes, the nitrogen flow was increased to 78 sccm (1.3×10$^{-6}$ m$^3$/s). After 20 minutes, the HF flow was increased to 62 sccm (1.0×10$^{-6}$ m$^3$/s) and the nitrogen was set to 1 sccm (1.7×10$^{-8}$ m$^3$/s). This condition was maintained for two hours, and then the temperature of the reactor was cooled to 190° C.

Fluorination of the HCFC Mixture

A mixture of 18.4% CF$_3$CH$_2$CCl$_2$F (HCFC-234fb), 36.2% CF$_3$CH=CCl$_2$ (HCFC-1225za), and 45.4% CCl$_2$FCH$_2$CCl$_2$F (HCFC-232fa) was fed to the above catalyst at 191 to 209° C. The flow rate of the above mixture was 1.8 sccm (3.0×10$^{-8}$ m$^3$/s) and the flow of HF was 57.6 sccm (9.6×10$^{-7}$ m$^3$s). Under these conditions, all of the HCFC-234fb and HCFC-232fa reacted. The gas chromatographic analysis of the reactor effluent at three temperatures is given in TABLE VI.

TABLE VI

| Ex. No. | Temp., ° C. | Product Analysis, GC Area % | | |
|---|---|---|---|---|
| | | 236fa | 235fa | 1223za |
| 10 | 191 | 93.0 | 6.9 | 0.1 |
| 11 | 201 | 99.0 | 1.0 | 0 |
| 12 | 209 | 99.9 | 0.1 | 0 |

Examples 13-15

Vapor Phase Fluorination of a Mixture of HCFC-1223za, HFC-234fb, and HFC-232fa

Catalyst Activation

A 15 in×⅜ in Inconel® tube was filled with 1.95 grams (1.5 cc) of a chromium oxide catalyst made via the pyrolysis of ammonium dichromate ground to 20-30 mesh. The catalyst was activated by first drying at 400° C. under a nitrogen purge followed by treatment with HF as described in EXAMPLES 10-12

Fluorination of the HCFC Mixture

The mixture used in EXAMPLES 10-12 was fed to the above catalyst at 190 to 210° C. The flow rate of the above mixture was 1.8 sccm (3.0×10$^{-8}$ m$^3$/s) and the flow of HF was 57.6 sccm (9.6×10$^{-7}$ m$^3$/s). Under these conditions, all of the HCFC-234fb and HCFC-232fa reacted. The gas chromatographic analysis of the reactor effluent at three temperatures is given in TABLE VII.

TABLE VII

| Ex. No. | Temp., ° C. | Product Analysis, GC Area % | | |
|---|---|---|---|---|
| | | 236fa | 235fa | %1223za |
| 13 | 190 | 84.1 | 15.6 | 0.3 |
| 14 | 201 | 96.9 | 3.1 | 0.03 |
| 15 | 209 | 99.4 | 0.6 | 0 |

What is claimed is:

1. A process for the preparation of 1,1,1,3,3,3-hexafluoropropane, comprising:
    (a) contacting at least one halopropane of the formula CF$_3$CH$_2$CH$_y$X$_{3-y}$, wherein each X is independently selected from the group consisting of F, Cl and Br, and y is 3, 2, or 1, with Cl$_2$ in the liquid phase in the presence of light or a free radical initiator to produce a mixture comprising CF$_3$CH$_2$CCl$_y$X$_{3-y}$;
    (b) contacting the CF$_3$CH$_2$CCl$_y$X$_{3-y}$ produced in step (a) with HF, optionally in the presence of a fluorination catalyst, to produce a product mixture comprising CF$_3$CH$_2$CF$_3$; and
    (c) recovering CF$_3$CH$_2$CF$_3$ from the mixture produced in step (b).

2. The process of claim 1 wherein in step (a) the halopropane of the formula CF$_3$CH$_2$CH$_y$X$_{3-y}$ is contacted with Cl$_2$ in the presence of light having a wavelength of from about 250 nm to about 400 nm.

3. The process of claim 2 wherein step (a) is carried out in a reactor wherein a portion of the reactor wall is fabricated from poly(tetrafluoroethylene), and wherein the light is transmitted through the poly(tetrafluoroethylene) portion.

4. The process of claim 2 wherein step (a) is carried out in a reactor wherein a portion of the reactor wall is fabricated from a copolymer of perfluoro(alkyl vinyl ether), and wherein the light is transmitted through the copolymer portion.

5. The process of claim 2 wherein step (a) is carried out in a reactor wherein a portion of the reactor wall is fabricated from a functionalized copolymer of terminally functionalized perfluoro(alkyl vinyl ether), and wherein the light is transmitted through the functionalized copolymer portion.

6. The process of claim 1 wherein in step (b) the contact with HF is carried out in the presence of a fluorination catalyst comprising trivalent chromium.

7. The process of claim 1 wherein the halopropane starting material is photochlorinated at a temperature controlled so that the halopropane starting material and chlorine are primarily in the liquid phase.

8. The process of claim 1 wherein the halopropane starting material is photochlorinated in the presence of a solvent capable of dissolving at least one compound selected from the group consisting of the halopropane starting materials and the step (a) products.

9. The process of claim 8 wherein in step (a) CF$_3$CH$_2$CClF$_2$ is produced from CF$_3$CH$_2$CHF$_2$ starting material.

10. The process of claim 9 wherein in step (b) CF$_3$CH$_2$CClF$_2$ is contacted with HF in the presence of a fluorination catalyst comprising trivalent chromium.

11. The process of claim 7 wherein the halopropane starting material is photochlorinated in a reactor provided with means for keeping halopropane starting materials in the liquid state while permitting HCl released during the chlorination to escape the reactor.

12. The process of claim 11 wherein step (a) is carried out in a reactor wherein a portion of the reactor wall is fabricated from poly(tetrafluoroethylene), and wherein the light is transmitted through the poly(tetrafluoroethylene) portion.

13. The process of claim 12 wherein in step (a) the halopropane of the formula $CF_3CH_2CH_yX_{3-y}$ is contacted with $Cl_2$ in the presence of light having a wavelength of from about 250 nm to about 400 nm.

14. The process of claim 11 wherein step (a) is carried out in a reactor wherein a portion of the reactor wall is fabricated from a copolymer of perfluoro(alkyl vinyl ether), and wherein the light is transmitted through the copolymer portion.

15. The process of claim 14 wherein in step (a) the halopropane of the formula $CF_3CH_2CH_yX_{3-y}$ is contacted with $Cl_2$ in the presence of light having a wavelength of from about 250 nm to about 400 nm.

16. The process of claim 11 wherein step (a) is carried out in a reactor wherein a portion of the reactor wall is fabricated from a functionalized copolymer of terminally functionalized perfluoro(alkyl vinyl ether), and wherein the light is transmitted through the functionalized copolymer portion.

17. The process of claim 16 wherein in step (a) the halopropane of the formula $CF_3CH_2CH_yX_{3-y}$ is contacted with $Cl_2$ in the presence of light having a wavelength of from about 250 nm to about 400 nm.

18. The process of claim 3 wherein the halopropane starting material is photochlorinated in the presence of a solvent capable of dissolving at least one compound selected from the group consisting of the halopropane starting materials and the step (a) products.

19. The process of claim 4 wherein the halopropane starting material is photochlorinated in the presence of a solvent capable of dissolving at least one compound selected from the group consisting of the halopropane starting materials and the step (a) products.

20. The process of claim 5 wherein the halopropane starting material is photochlorinated in the presence of a solvent capable of dissolving at least one compound selected from the group consisting of the halopropane starting materials and the step (a) products.

* * * * *